United States Patent [19]

Tschaen et al.

[11] Patent Number: 5,145,957
[45] Date of Patent: Sep. 8, 1992

[54] STEREOSELECTIVE SYNTHESIS OF A CHIRAL CIS 3-BETA HYDROGEN (3R) 4-AROYLOXY AZETIDINONE

[75] Inventors: David M. Tschaen, Aberdeen; Joseph E. Lynch, Plainfield; William L. Laswell, Bridgewater; Ralph P. Volante, East Windsor; Ichiro Shinkai, Westfield, all of N.J.

[73] Assignee: Merck & Co., Inc., Rahway, N.J.

[21] Appl. No.: 819,601

[22] Filed: Jan. 9, 1992

Related U.S. Application Data

[63] Continuation of Ser. No. 644,866, Jan. 23, 1991, abandoned, which is a continuation of Ser. No. 522,416, May 10, 1990, abandoned, which is a continuation of Ser. No. 169,650, Mar. 18, 1988, abandoned.

[51] Int. Cl.$^5$ .................. C07B 37/10; C07D 205/08; C07F 7/18
[52] U.S. Cl. ............................... 540/200; 540/357
[58] Field of Search ........................ 540/357, 200

[56] References Cited

U.S. PATENT DOCUMENTS 4,556,514 12/1985 Sunagawa ..................... 540/200
4,556,515 12/1985 Yamamoto ..................... 564/454

FOREIGN PATENT DOCUMENTS 0171064 2/1986 European Pat. Off. .
0167155 11/1986 European Pat. Off. .
269236 6/1988 European Pat. Off. .
3522081 1/1986 Fed. Rep. of Germany .
2144419A 7/1984 United Kingdom .
2162840 6/1985 United Kingdom .

OTHER PUBLICATIONS

Hubschwerten et al., Helv. Chem. Acta 66, 2206 (1983).
Sharma et al., Indian J. Chem 19B, 760 (1980).
Just et al., Can J. Chem 56, 2720 (1978).
Bose, I., J.C.S. Perkins I, p. 1880 (1925).
Bose II, Tetrahedron 37, 2321 (1981).
Aizpurua, Tet. Letters 37, 4359 (1980).
H. Staudinger et al., Chem. Ber., 1911, 44, pp. 365–374.
Reider et al., Tetrahedron Letters, vol. 23, No. 22, pp. 2293–2296 (1982).
Gunda George, Tetrahedron Letters, vol. 25, No. 35, pp. 3779–3782 (1984).
M. Shiozaki et al., Tetrahedron Letters, vol. 40, No. 10, pp. 1795–1802 (1984).
Iimori et al., Tetrahedron Letters, vol. 27, No. 19, pp. 2149–2152 (1986).
Euchem 1984, Por-Camargue (France) 1984, M. Colombo et al.
Evans et al., Tetrahedron Letters, vol. 26, No. 32, pp. 3787–3790 (1985).
Evans et al., Tetrahedron Letters, vol. 26, No. 32, pp. 3783–3786 (1985).
Georg et al., JACS, (1987), 109, pp. 1129–1135.
Shiozaki et al., Tetrahedron Letters, vol. 22, No. 51, pp. 5205–5208 (1981).
Iimori et al., Tetrahedron Letters, vol. 26, No. 12, pp. 1523–1526 (1985).
Hart et al., Tetrahedron Letters, vol. 26, No. 45, pp. 5493–5496 (1985).
Bose, et al., Tetrahedron Letters, vol. 27, No. 49, pp. 5955–5958 (1986).
Alcaide et al. Heterocycles, vol. 24, No. 6, 1986 pp. 1579–1583.
Karady et al., JACS, (1981), pp. 6765–6767.
Hanessian et al., JACS (1985) 107, pp. 1438–1439.
Mukerjee et al., Synthesis, No. 6 (1973) pp. 327–346.
Georg et al., Tetrahedron Letters, vol. 26, No. 33, pp. 3903–3906 (1985).
Farrar, Res. Chem. Prog., vol. 29, pp. 85–101 (1969).
Translation of DE 3620467.

*Primary Examiner*—Mark L. Berch
*Attorney, Agent, or Firm*—Curtis C. Panzer; Robert J. North

[57] ABSTRACT

A process is described for the stereocontrolled synthesis of (3R,4R)-3-[(1R)-1-hydroxyethyl]-4-benzoyloxyazetidin-2-ones and their derivatives by cycloaddition involving an imine and a ketone, generated from 3(S)-hydroxybutyrate which are useful intermediates in the synthesis of carbapenem antibiotics.

10 Claims, No Drawings

STEREOSELECTIVE SYNTHESIS OF A CHIRAL CIS 3-BETA HYDROGEN (3R) 4-AROYLOXY AZETIDINONE

This is a continuation of application Ser. No. 07/644,866, filed Jan. 23, 1991, abandoned, which is a continuation of application Ser. No. 522,416, filed May 10, 1990, now abandoned, which is a continuation of application Ser. No. 169,650, filed Mar. 18, 1988, abandoned.

BACKGROUND OF THE INVENTION

1. Field of the Invention

This invention relates to a stereo-controlled process for producing 3-beta hydrogen (3R) 4-aroyloxy azetidinone intermediates in high yield having desired chirality which are essential in carbapenem synthesis.

2. Brief Description of Disclosures in the Art

Carbapenem antibiotics, particularly thienamycin and imipenem (see U.S. Pat. Nos. 3,950,377 and 4,194,047) are well known for treating a broad spectrum of gram-negative and gram-positive bacterial infections.

Processes for synthesis of these type antibacterial agents are well known in the art as witness the following patents issued inter alia to Merck & Co.; U.S. Pat. Nos. 4,543,257, 4,234,596 and 4,232,030.

In order to develop, faster, less expensive and better methods for their production, research is continually being carried out in this area. One focus in this field has been on the ketene-imine cycloaddition mode of synthesis of the starting azetidinone intermediates. Particularly desired is a process which produces the initial azetidinone intermediate having a 3-beta hydrogen in high yields. (See following Structure III having a 3-position beta hydrogen. According to the commonly used R/S stereochemical designations, when A in Structure III is aryl, the 3-position is (3S) and when A is aroyloxy, it is (3R), in which the 3-hydrogen remains in the beta stereoconfiguration.)

The cycloaddition of an imine and a ketene to product azetidinones is known in the art, e.g. H. Staudinger and S. Jologin, *Chem. Ber.*, 1911, 44 p. 373.

Recently there has been considerable interest in ketene-imine cycloaddition chemistry in the use of β-hydroxybutyric acid as a readily available, chiral starting material. This reagent has been used in enolate condensations with imines to generate β-lactam intermediates; however, these approaches typically provide modest yields of condensation products and require extensive functional group manipulation in order to liberate the desired C-4 acetoxy azetidinone species, a functionality necessary for rapid conversion to useful carbapenems. See Georg, G.I., Kant, J., Gill, H.S., *J. Am. Chem. Soc.* 1987, 109, 1129; Hart, D.J., Ha, D.C., *Tetrahedron Lett.* 1985, 5493; Iimori, T., Shibasaki, M., *Tetrahedron Lett.* 1985, 1523; Giuanti, G., Narisano, E., Banfi, L., *Tetrahedron Lett.* 1986, 5955; Ohasi, T., Kan, K., Sada, I., Miyama, A., Watanabe, K., Eur. Pat. Appln. EP 167155. 1986; Aizpurya, J.M., Cossio, F.P., Lecea, B., Palomo, C., *Tetrahedron Lett.* 1986, 4359; Alcaide, B., Dominguez, G., Escobar, G., Parreno, V., Plumet, J., *Heterocycles* 1986, 24. 6; and Bose, A.K., Krishnan, L., Wagle, D.R., Manhas, M.S., *Tetrahedron Lett.* 1986, 5955. The above references are hereby incorporated by reference.

What is desired in the art is a process for producing 3-beta hydrogen (3S)-3-(1-hydroxylethyl)-4-aroyl azetidinones in high yield.

SUMMARY OF THE INVENTION

It has been found that by reacting an 3-(S)-hydroxybutyrate with an imine, being an N-protected, C-acyl, -aryl, -aryloxy, or acyloxyimine, under anhydrous conditions at low temperature during which the chiral butyrate compound is initially converted in situ to a transient ketene intermediate and then allowed to undergo a ketene-imine cycloaddition under mild conditions, there is directly obtained an azetidinone intermediate with the requisite stereochemistry at C-3(beta-hydrogen), required for carbapenem synthesis. Conversion of this intermediate directly to the 5(R), 3(R) benzoyloxy carbapenem intermediate then follows standard procedures.

In accordance with this invention there is provided a process for preparing the chiral azetidinone compound:

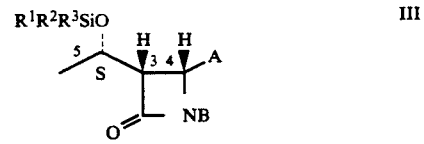

comprising the step of contacting the chiral butyryl compound:

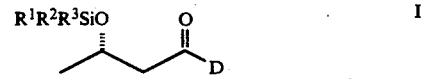

with the imine:

in an organic solvent therefor and in the presence of an organic amine capable of generating a ketene from the butyryl compound; in the temperature range of −60° C. to +120° C., for a sufficient time to yield the desired 3(S) azetidinone III (3-β-hydrogen); wherein $R^1$, $R^2$ and $R^3$ are independently selected from $C_1$–$C_5$ alkyl or aryl, optionally substituted with groups inert under the reaction conditions with the proviso that all three groups are not methyl; D is halo, or an effective organic leaving group under the reaction conditions; B is an imine-nitrogen protecting group removable by oxidation, acid hydrolysis or catalytic hydrogenation under mild conditions; A is $C_1$–$C_5$ linear or branched acyl or $C_6$–$C_8$ aroyl, which can optionally be substituted by groups inert under the reaction conditions, such as acyloxy or aryloxy.

DESCRIPTION OF THE INVENTION AND PREFERRED EMBODIMENTS

The process of the invention can easily be described and understood by referring to the following Flow Chart A.

Compound I, being the butyryl compound, first having been converted to a ketene intermediate, "I-Ketene" e.g. by contacting with an organic base, e.g. diisopropyethylamine in anhydrous methylene chloride at −40° C., is reacted, for example, in the same solvent at −40° C. with the imine II. Generation of the ketene intermediate followed by reaction with imine II results in two diastereoisomers: the desired cis azetidinone III (3-β-hydrogen) and the other cis isomer IIIa (3-α-hydrogen). Generally, the condensation step involves cis addition with very little trans isomer being formed. Separation of the desired (III) from the crystalline mixture of both diastereoisomers by fractional crystallization followed by treatment of the resulting cis (3-β-hydrogen) isomer III, for example, with butyl ammonium fluoride in THF at room temperature, removes the silyl protecting group and epimerizes the C-4 hydrogen to form compound IV. Treatment of IV, for example, under Mitsonobu conditions (see O. Mitsonobu; Synthesis, 1981, 1; and references therein) with triphenylphosphine, formic acid and diisopropylazodicarboxylate epimerizes the 5-(S) hydroxyethyl group to 5(R) to form V. Treatment of V, for example, with ceric (IV) ammonium nitrate to remove the N-protecting group results in compound VI. Treating compound VI, for example, with meta-chloroperbenzoic acid by the known Baeyer-Villiger oxidation then results in the desired intermediate VII.

Flow Chart B illustrates conversion of VII to the well-known carbapenem bicyclic ketoester intermediate, IX, as described in U.S. Pat. No. 4,318,912, hereby incorporated by reference for this particular purpose.

FLOW CHART A

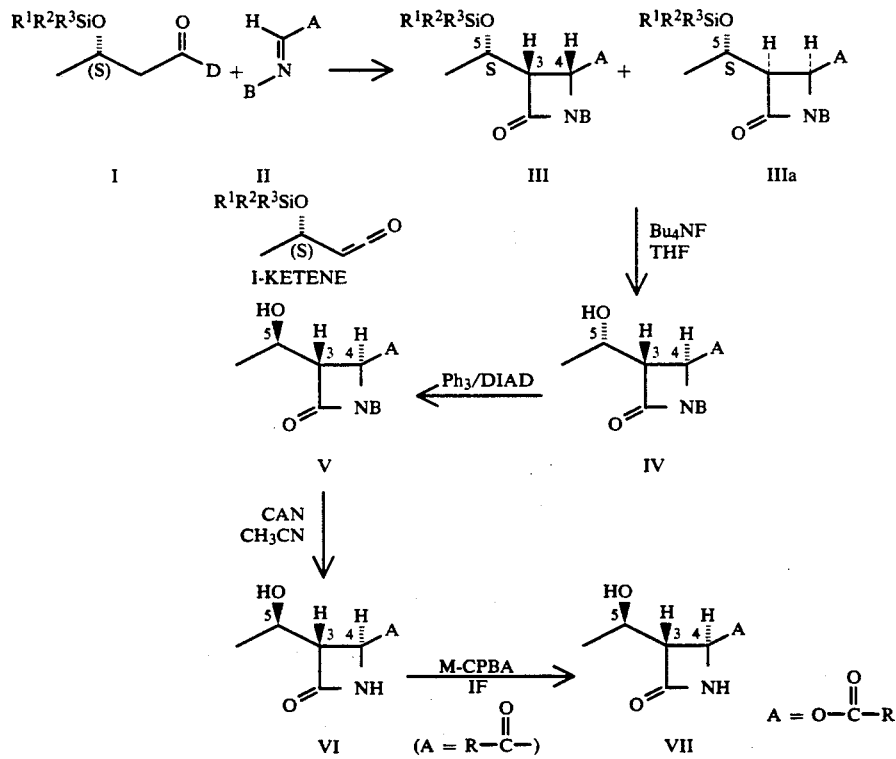

FLOW CHART B

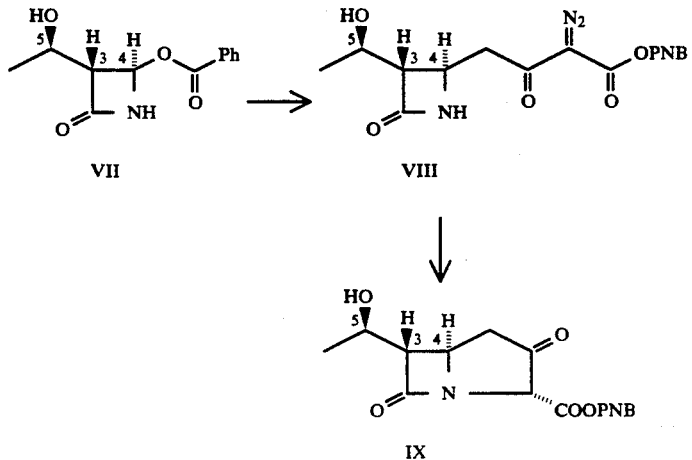

The above flow chart establishes utility for the intermediates formed by this process in relation to the main carbapenem intermediate in forming carbapenem antibiotics, i.e. thienamycin and imipenem.

Included in the description of structure I, the chiral butyrate compound, is the requirement that this compound be capable of forming a ketene in solution in the presence of an organic amine base. For this invention it is required that carbon-3 of the butyrate be in the S stereoconfiguration. The hydroxy group in the 3-position can be protected by a bulky silicon protecting group which is used in the antibiotic art, e.g. see U.S. Pat. No. 4,196,211, which is hereby incorporated by reference for this particular purpose.

$R^1$, $R^2$, $R^3$ are independently selected from $C_1$–$C_5$ linear or branched alkyl or aryl, optionally substituted by groups which are chemically inert under the reaction conditions in the invention process, with the proviso that $R^1$, $R^2$ and $R^3$ are not simultaneously all methyl, i.e., trimethylsilyl. It has been found that a "bulky" silyl protecting group, i.e. larger than trimethylsilyl, leads to higher III/IIIa molar ratios in the condensation of I and II, presumably through some of steric influence when using the S-butyrate I. Ratios of III $3\beta$BH/$3\alpha$H are in the range of about 1:1 when using trimethylsilyl and increase progressively as the steric bulk of the protecting group increases to dimethyl-t-butylsilyl, 60:40; diphenyl-t-butylsilyl, 60:40 and then triisopropylsilyl (TIPS) yielding a $3\beta$BH/$3\alpha$H molar ratio of 6–7:1. Representative examples of $R^1$, $R^2$, $R^3$ groups include methyl, ethyl, iso-propyl, butyl, sec.-butyl, tert.-butyl, and pentyl; and aryl, which can be phenyl and substituted phenyl, wherein the phenyl substituents which can be meta or para include e.g. methoxy, chloro, or nitro, which do not interfere with the desired reaction. Preferred silyl protecting groups include dimethyl-t-butylsilyl, phenyldimethylsilyl, benzyldimethylsilyl, triisopropylsilyl, tribenzylsilyl, triphenylsilyl, and the like. A particularly preferred silyl protecting group is triisopropylsilyl.

D is chosen from: halo, including chloro, bromo and fluoro; OP=O(OPh)$_2$; imidazole; or O(C=O)$R^1$, where $R^1$ is branched $C_3$–$C_4$ alkyl, i.e. t-butyl. Ph is phenyl. Preferred is where D is chloro. The particular group D has the characteristic in that it is functionally an effective organic leaving group capable of generating a ketene when the butyrate compound is contacted with an organic base.

The starting 3-(S)(−)-hydroxybutyric acid, is commercially available from Aldrich Chemical Co. Also, the butyryl compound can be made according to the well-known methods as described in the art, e.g., Seebach, D.; Imwinkelried, R.; Studky, G.; *Angew. Chem., Int. Ed.*, 1986, 25, 178. Seebach, D.; Zuger, M.F.; *Helv. Chim. Acta.* 1982, 65, 495.

The imine II is preferably of the structure as indicated where the substituents A and B are trans to one another on the imine. The imine can also be in the cis configuration, but for convenience, the structure is drawn in the trans form, but is understood to be either cis, trans, or mixtures thereof. However, the imine must be in the trans form to give the desired cis-$\beta$-lactam III.

B is a conventional nitrogen-protecting group which is removable by conventional procedures, for example, by mild acid hydrolysis, by conventional ceric ammonium nitrate oxidative cleavage, or by catalytic hydrogenation such as Raney nickel catalysis in ethanol. Representative examples of B substituents include para-methoxyphenyl, p-t-butoxyphenyl, 3,4-dimethoxyphenyl, 2,4-dimethoxyphenyl, 3,5-dimethylphenyl, and the like. Preferred is para-methoxyphenyl.

Group A is acyl, aryl, acyloxy or aroyloxy, of the formula;

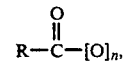

where n is 0 or 1 and R is a $C_1$–$C_5$ linear or branched alkyl or $C_6$–$C_{11}$ aryl, heterocyclic group, optionally substituted with electron-donating or electron-withdrawing substituents which do not interfere in the process including halo, nitro, alkoxy, i.e. chloro or methoxy. Representative examples include methyl, ethyl, iso-propyl, butyl, pentyl, phenyl, and the like. Preferred in the reaction is phenyl or methyl.

Procedures for making the imine involve condensations between an aldehyde or its equivalent and primary amine and are described in the literature, for example, in Farrar, Rec. Chem. Prog. 29, 85–101 (1968), hereby incorporated by reference for this particular purpose.

The process of the instant invention is carried out generally by first generating the ketene (I) in situ in solution, since it is unstable, by reaction of the butyryl structure I with an organic base. If the butyryl compound is an acid chloride it can be made directly from the corresponding acid by reaction with chlorinating agents such as oxalyl chloride, thionyl chloride, and the like, neat in liquid solution or in a solvent such as dichloromethane at low temperature such as 0° C. to room temperature under anhydrous conditions. If the butyryl compound is an ester containing leaving group D, it is used directly, in the presence of the organic imine in solution to generate the ketene.

The organic amine which is used in the ketene generating process is a nitrogen-containing organic amine which can be a conventional trialkylamine, triarylamine, or mixed types such as monoaryldialkylamine, heteroaryl dialkylamine, nitrogen heteroarylamine and the like. Representative organic nitrogen-containing amines include triethylamine, trimethylamine, methyldiethylamine, methyldiisopropylamine, pyridine, quinoline, N-methylpyrrolidine, N,N'-dimethylpiperazine and the like. Preferred is diisopropylethylamine.

The ketene generation method can be conducted in an inert organic solvent such as $C_1$–$C_4$ halogenated hydrocarbon, containing 1–4 halogen atoms, $C_2$–$C_5$ straight chain or cyclic ethers, or alkyl nitriles with the stipulation that they contain no reactive functional group which would interfere with the reaction and that the reaction conditions are carried out under anhydrous conditions. Representative examples include halogenated alkanes, alkyl and cycloalkyl ethers and alkyl nitriles including dichloromethane, diethyl ether, acetonitrile, tetrahydrofuran, dioxane and the like. Preferred is dichloromethane.

The reaction is generally conducted in temperature range of about −40° to +60° C., preferably in the range of −40° to +25° C. Generally, the ketene generation is conducted at lower temperatures and the imine condensation allowed to proceed at slightly higher temperatures.

The reaction can be conducted at atmospheric pressure or under a slight vacuum up to several pressures. Preferred is atmospheric pressure.

Following the generation of the ketene in situ, the imine is generally combined there with the solution in a solvent and the ketene-imine reaction allowed to occur under anhydrous conditions at a very fairly low temperature being −20° to room temperature. The reaction can require anywhere from 15 minutes to 1 hour or even longer depending on the desired yield under mild conditions and anhydrous conditions in order to allow the ketene-imine reaction to go to its completion. Various modifications of carrying out the reaction procedure can be utilized including adding the organic amine to the butyryl compound-imine mixture, or adding the organic amine to the butyryl compound, then adding the imine or adding the formed ketene to the imine, and the like. Preferred is where the ketene is formed initially and then the imine added subsequently.

Generally, the obtained azetidinone structure III containing the desired 5(S), 3-β-hydrogen) stereochemistry is obtained in about 85% yield. Both cis isomers 3-(βH) III and 3-(αH) IIIa are obtained in a III/IIIa ratio of about 7:1, in which the desired 3-(ββH) isomer, being isomer III, can be separated by standard methods known in the art, including fractional crystallization, column chromatography or high pressure liquid chromatography. The desired isomer 3-(βH) III is then separated from the reaction mixture and then the hydrogen at ring position 4 is converted to the alpha configuration while the silyl protecting group is removed; the nitrogen protecting group is cleaved; and the compound subjected to a Baeyer-Villiger reaction to derive Compound VII which is the prime intermediate leading to the condensation reaction. Details and examples of these specific processes are given in the following examples.

Standard apparatus used in the art is useful for carrying out the claimed invention.

The following examples are indicative of carrying out the invention as regarded by as and should not be construed as being limitations on the scope or spirit of the instant invention.

EXAMPLE 1

Step A. Methyl-(S)-3-(triisopropylsilyloxy)butyrate

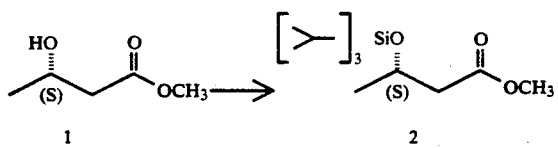

Materials

| | |
|---|---|
| Methyl-(S)-3-hydroxybutyrate (1) (MW = 118.13) | 5.0 g, 0.04 mol |
| Triisopropylsilyltrifluoromethane sulfonate (TIPS-TFMS) (MW = 306.42) | 14.78 ml, 0.05 mol |
| 2,6-Lutidine (MW = 107.16) | 12.32 ml, 0.1 mol |

A mixture of 5.0 g (0.04 mol) of 1, methyl-(S)-3-hydroxybutyrate, 14.78 ml (0.05 mol) TIPS-TFMS, 12.32 ml (0.1 mol) 2,6-lutidine in 100 ml of methylene chloride was stirred at 0° C. for 2 hours. To the resultant mixture was added 50 ml of mixed hexanes and extracted (50 ml) with cold 1N HCl, dried over anhydrous NaSO4 and concentrated in vacuo. The crude product 2, 10.9 g, (100%) was used without further purification.

H-NMR (300 MHz, CDCl$_3$) 1.05 (18H,s), 1.05 (3H,m), 1.24 (3H,d,J=6.2Hz), 2.48 (2H,m) 3.64 (3H,s), 4.38 (1H,m).

Step B. 3-(S)-(triisopropylsilyloxy)butanoic Acid

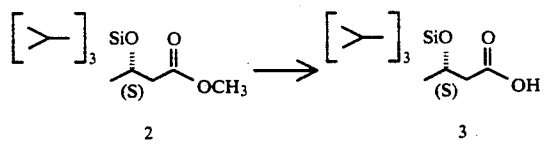

Materials

| | |
|---|---|
| (S)-TIPS-HOBA (MW = 274.1) (2) | 7.5 g, 0.027 mol |
| LiOH (1.03M) | 160 ml, 0.165 mol |

To magnetically stirred mixture of 7.5 g (0.027 mol) of 2, (S)-TIPS-HOBA, in 150 ml of THF and 150 ml H$_2$O, was added 1.75 g (0.04 moles) LiOH. The reaction mixture was heated at 50° C. for 8 hours. After cooling to room temperature, 100 ml of ether was added and the phases separated. The aqueous layer was acidified to PH=3 with concentrated HCl. The aqueous layer was extracted with ether (2×100 ml), organic layers combined, dried over MgSO$_4$ and concentrated in vacuo to afford 6.2 g of 3 (87%) which was used without further purification.

H-NMR (300 MHz, CDCl$_3$) del 1.05 (18H,s) 1.05 (3H,m) 1.28 (3H,d,J=6.2 Hz), 2.54 (2H,M), 4.39 (1H,m).

Step C. (S)-3-(Triisopropylsilyloxy)butyryl Chloride

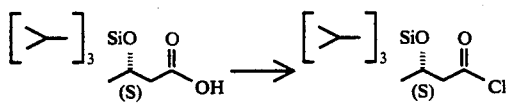

Materials

| | |
|---|---|
| TIPS-HOBA (MW = 260) (3) | 5.5 g, 0.021 mol |
| Oxalyl chloride (MW = 129.93, d = 1.445) | 3.7 ml, 0.042 mol |

To the TIPS-HOBA 3 in 100 ml methylene chloride was added dropwise the oxalyl chloride at room temperature controlling the evolution of gas (CO$_2$). After 2 hours stirring at room temperature, the excess oxalyl chloride was removed with a sweep of nitrogen to yield 5.5 g (93%) acid chlorine 4, which was used without subsequent purification.

H-NMR (300 MHz, CDCl$_3$) δ1.05 (18,s), 1.05 (3H,m), 1.29 (3m,d,J=6.2 Hz), 3.05 (2H,m), 4.45 (1H,m).

Step D. Ketene-Imine Addition

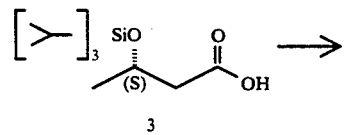

9

-continued

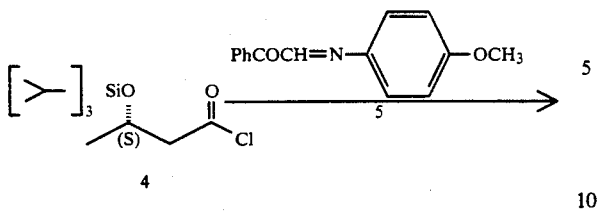

4

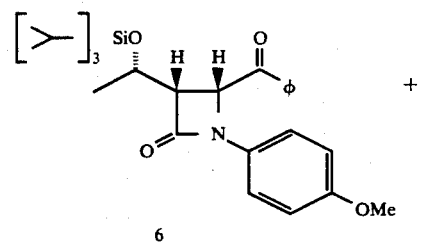

6

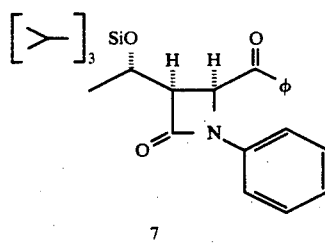

7

The acid chloride 4 was generated following procedure C. This unpurified acid chloride was employed in the subsequent cyclo-addition. To a solution of 2.1 g (0.0075 mol) of the acid chloride 4 in 30 ml CH₂Cl₂, cooled to −40° C., was added 1.94 ml (0.011 mol) of iPr₂NEt followed by 2.32 g (0.009 mol) of the imine 5. (Imine 5 produced by the procedure of Alcaide, B.; Dominquez, G.; Escobar, G.; Parreno, V.; Plumet, J. *Heterocycles*, 1986, 24, 6.) After 1 hour stirring at −40° C., the cooling bath is adjusted and the reaction is held at −20° C. for 18 hours. The mixture was concentrated in vacuo to yield lactam diastereoisomers 6 and 7. The two product diastereomers were easily separable by flash chromatography on silica gel with an Rf difference of ca 0.2 in 1:6 EtOAc-hexanes to yield 1.70 g 6 and 0.31 g of 7. The diastereomeric mixture of 6:7 was determined by 300 MHz H-NMR to be 7:1.

EXAMPLE 2

Step E. Amide Nitrogen Deprotection

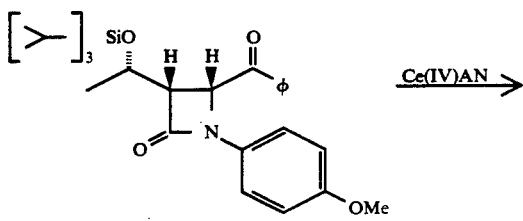

10

-continued

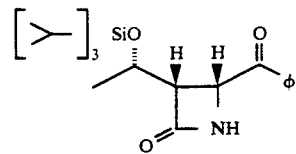

8

The diastereoisomer 6 was subjected to oxidative dearylation with ammonium cerium (IV) nitrate, (Ce IV A.N.) to obtain the NH β-lactam 8 following the literature procedure of Hanessian et al., *J. Am. Chem. Soc.* 1985, 107, 1438-1439. A solution of 5.13 g (0.0032 moles) of ceric ammonium nitrate in 30 ml of acetonitrile was added dropwise to a solution of 1.5 g (0.009 moles) of β-lactam 6 in 100 ml acetonitrile at −20° C. The mixture was warmed to room temperature, stirred for 1 hour, then poured into 100 ml saturated NaHCO₃ and extracted with methylene chloride. The organics were dried over Na₂SO₄ and concentrated. The residue was flash chromatographed on silica gel eluting with ethyl acetate:hexane (1:2) to provide 0.410 g of the product β.

Step F. Silyl nBu₄NF Deprotection

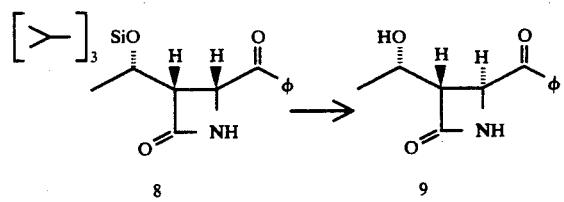

To 0.20 g (0.5 mmol) of the crude reaction product 8 previously obtained in step E in 1.0 ml of THF was added 1.22 ml (2.4 equivs.) of (1 M) n-Bu₄NF (tetra n-butylammonium fluoride) in THF at 0° C. The mixture was warmed to room temperature, stirred for 0.75 hour, concentrated in vacuo, and purified by preparative chromatography eluting with ethyl acetate:hexane (70:30) to yield 0.049 g (42%) of the trans-diastereomeric β-lactam 9.

Step G. Mitsonobu Reaction and Baeyer-Villiger Oxidation

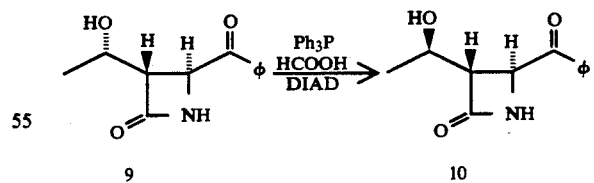

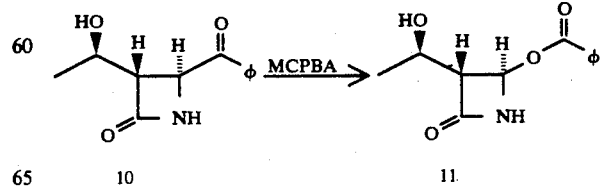

Inverted Alcohol 10: Formic acid (0.017 ml) and triphenylphosphine (0.06 g) were added to a solution of 0.020 g (0.09 mmol) of β-lactam 9 in 4 ml of methylene chloride at 0° C. (DIAD) Diisopropylazodicarboxylate (0.045 mol) was added and the mixture was slowly warmed to room temperature and stirred for an additional 15 hours. The mixture was cooled to 0° and 1 ml of methanol and 1 ml of methanol:water/hydrochloride acid (7:3:1) was added. After stirring at room temperature for 2 hours the mixture was washed with water and extracted with methylene chloride. The organics were dried over $Na_2SO_4$, purified by preparative tlc eluting with ethyl acetate:hexane (2:1) to provide 18 mg (90%) of inverted β-lactam 10.

Benzoate 11: A mixture of 0.021 g (0.1 mmole) of β-lactam 10 and 0.025 (0.15 mmole) of m-chloroperbenzoic acid (MCPA) in 5 ml of methylene chloride were stirred at room temperature for 3 hours. An additional 0.015 g of m-chloroperbenzoic acid was added and the reaction stirred an additional 3 hours. The mixture was filtered, concentrated in vacuo and purified by preparative tlc eluting with ethyl acetate:hexane (2:1) to provide 0.015 g (68%) of the β-lactam 11.

NMR for compound 6: $^1$H NMR ($CDCl_3$,300 MHz), 0.90 (18H,s), 0.90 (3H,m), 1.34 (3H,d,J=6.4 Hz), 3.77 (3H,s), 3.93 (1H,dd,J=3.8,6.3 Hz), 4.31 (1H,m), 5.40 (1H,d,J=6.3 Hz), 6.83 (2H,d,J=9.1), 7.24 (2H,d,J=9.1 Hz), 7.52 (2H,dd,J=7.1,7.4 Hz), 7.63 (1H,dd,J=7.4,7.4 Hz), 8.01 (2H,d,J=7.1 Hz).

What is claimed is:

1. A process for preparing the chiral azetidinone compound:

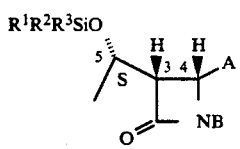

in at least a 60:40 ratio to its 3-α-hydrogen diastereomer, comprising the step of contacting the chiral butyryl compound:

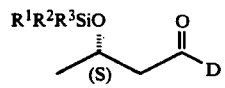

with the imine:

in an organic solvent therefor and in the presence of an organic amine capable of generating a ketene from the butyryl compound; in the temperature range of −60° C. to +120° C., for a sufficient time to yield the desired azetidinone III; where $R^1$, $R^2$ and $R^3$ are independently selected from $C_1$-$C_5$ alkyl or aryl, optionally substituted with groups inert under the reaction conditions with the proviso that at least one of $R^1$, $R^2$ or $R^3$ is t-butyl or a bulkier group; D is halo, or an effective organic leaving group under the reaction conditions; B is an imine-nitrogen protecting group removable by oxidation, acid hydrolysis, or catlytic hydrogenation under mild conditions; A is $C_1$-$C_5$ linear or branched acyl or acyloxy, $C_6$-$C_8$ aroyl or aryloxy which can optionally be substituted by groups inert under the reaction conditions.

2. The process of claim 1 wherein the temperature is in the range of −40° to +60° C.

3. The process of claim 1 wherein the organic solvent is selected from halogenated alkanes, alkyl ethers, or cyclic ethers.

4. The process of claim 1 wherein the organic amine is selected from tri-$C_1$-$C_5$-alkylamines, N-alkylcycloalkylamines or heterocyclic amines.

5. The process of claim 1 wherein $R^1R^2R^3Si$ is selected from triisopropylsilyl, dimethyl-t-butyl-silyl or phenyldimethylsilyl.

6. The process of claim 1 wherein D is selected from chloro, bromo, iodo,

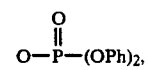

imidazolyl, or $-O-C=O(R^4)$ wherein $R^4$ is t-butyl.

7. The process of claim 1 wherein A is selected from acetyl, propionyl, benzoyl, acetoxy, propionate, or benzoyloxy.

8. The process of claim 1 wherein B is selected from p-methoxyphenyl, 2,4-dimethoxyphenyl, 3,5-dimethylphenyl or p-methoxybenzyl.

9. The process of claim 1 wherein the azetidinone is:

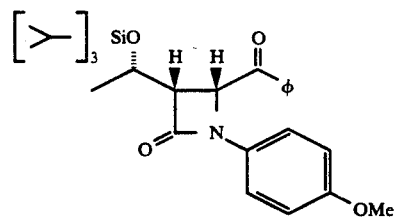

10. A process for producing the chiral azetidinone:

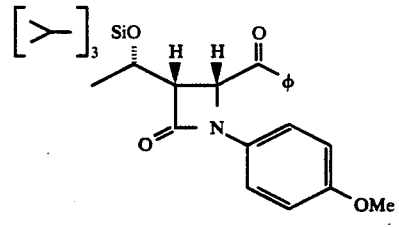

comprising the step of contacting the chiral butyryl compound:

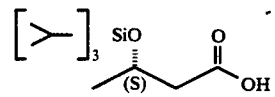

with oxalyl chloride at room temperature under anhydrous conditions to form the corresponding acid chloride:

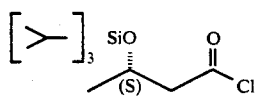
followed by contacting the formed acid chloride with
the imine:
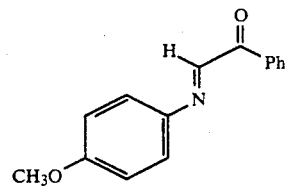
in dichloromethane solvent, at −40° C., in the presence of diisopropylethylamine, and conducting the reaction between the temperature range of −40° to 25° C. for a sufficient time to yield the desired chiral azetidinone.
* * * * *